US012406369B2

(12) United States Patent
Mirar

(10) Patent No.: US 12,406,369 B2
(45) Date of Patent: Sep. 2, 2025

(54) METHODS AND SYSTEMS TO EXCLUDE PERICARDIUM IN CARDIAC STRAIN CALCULATIONS

(71) Applicant: GE Precision Healthcare LLC, Wauwatosa, WI (US)

(72) Inventor: Hani Mirar, Oslo (NO)

(73) Assignee: GE PRECISION HEALTHCARE LLC, Wauwatosa, WI (US)

(*) Notice: Subject to any disclaimer, the term of this patent is extended or adjusted under 35 U.S.C. 154(b) by 580 days.

(21) Appl. No.: 17/657,676

(22) Filed: Apr. 1, 2022

(65) Prior Publication Data
US 2023/0316520 A1    Oct. 5, 2023

(51) Int. Cl.
| | | |
|---|---|---|
| G06T 7/00 | (2017.01) | |
| G06T 7/11 | (2017.01) | |
| G06T 7/246 | (2017.01) | |
| G06V 10/22 | (2022.01) | |
| G06V 10/26 | (2022.01) | |

(52) U.S. Cl.
CPC .............. *G06T 7/0014* (2013.01); *G06T 7/11* (2017.01); *G06T 7/248* (2017.01); *G06V 10/235* (2022.01); *G06V 10/26* (2022.01); *G06T 2207/10132* (2013.01); *G06T 2207/20104* (2013.01); *G06T 2207/30048* (2013.01); *G06V 2201/031* (2022.01)

(58) Field of Classification Search
CPC ......... G06T 7/0014; G06T 7/11; G06T 7/248; G06T 2207/10132; G06T 2207/20104; G06T 2207/30048; G06V 10/235; G06V 10/02; G06V 2201/031
See application file for complete search history.

(56) References Cited

U.S. PATENT DOCUMENTS

| | | | |
|---|---|---|---|
| 2015/0289840 A1* | 10/2015 | Konofagou | A61B 8/485 600/438 |
| 2019/0125309 A1 | 5/2019 | Ramm et al. | |
| 2020/0074625 A1 | 3/2020 | Østvik et al. | |
| 2020/0100768 A1 | 4/2020 | Torres et al. | |

FOREIGN PATENT DOCUMENTS

WO    WO-2019178404 A1 *  9/2019  ........... A61B 5/7267

OTHER PUBLICATIONS

De Craene, M. et al., "3D Strain Assessment in Ultrasound (Straus): A Synthetic Comparison of Five Tracking Methodologies," IEEE Transactions on Medical Imaging, vol. 32, No. 9, Sep. 2013, 15 pages.
Johnson, C. et al., "Practical tips and tricks in measuring strain, strain rate and twist for the left and right ventricles," Echo Research & Practice, vol. 6, No. 3, Jun. 13, 2019, 12 pages.

* cited by examiner

*Primary Examiner* — Matthew C Bella
*Assistant Examiner* — Jinsu Hwang
(74) *Attorney, Agent, or Firm* — McCoy Russell LLP

(57) ABSTRACT

Various methods and systems are provided for a medical imaging system. In one embodiment, a method comprises generating cardiac ultrasound images from ultrasound imaging data of a heart, excluding pericardium depicted in the cardiac ultrasound images, and calculating strain values of a myocardium region of interest in the cardiac ultrasound images while excluding the pericardium depicted in the cardiac ultrasound images. In this way, the strain values may be calculated more accurately by not including information from the non-contractile pericardium.

20 Claims, 9 Drawing Sheets

METHODS AND SYSTEMS TO EXCLUDE PERICARDIUM IN CARDIAC STRAIN CALCULATIONS

FIELD

Embodiments of the subject matter disclosed herein relate to ultrasound imaging.

BACKGROUND

An ultrasound imaging system typically includes an ultrasound probe that is applied to a patient's body and a workstation or device that is operably coupled to the probe. During a scan, the probe may be controlled by an operator of the system and is configured to transmit and receive ultrasound signals that are processed into an ultrasound image by the workstation or device. The workstation or device may show the ultrasound images as well as a plurality of user-selectable inputs through a display device. The operator or other user may interact with the workstation or device to analyze the images displayed on and/or select from the plurality of user-selectable inputs. As an example, the user may select a region of interest in cardiac ultrasound images from which strain values may be calculated.

BRIEF DESCRIPTION

In one aspect, a method can include generating cardiac ultrasound images from ultrasound imaging data of a heart, excluding pericardium depicted in the cardiac ultrasound images, and calculating strain values of a myocardium region of interest in the cardiac ultrasound images while excluding the pericardium depicted in the cardiac ultrasound images.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings, in which.

DETAILED DESCRIPTION

Embodiments of the present disclosure will now be described, by way of example, with reference to the FIGS. 1-11, which relate to various embodiments for cardiac ultrasound imaging. In particular, systems and methods are provided for determining strain values within a heart of a patient. The contraction and relaxation of cardiac muscles during each heartbeat results in longitudinal, circumferential, and radial strain values, which may be calculated via a strain tool used in cardiac ultrasound imaging (e.g., speckle tracking echocardiography). Such strain values may provide information on regions of the heart with impaired cardiac muscle function.

Speckle tracking echocardiography may include defining a region of interest (e.g., either automatically or manually set by a user) and tracking positional changes in brighter intensity pixel areas, known as speckles, over time. However, the calculated strain values may be inaccurate based on the tissue included in the region of interest. For accurate strain values, it is desired to include only the contractile myocardium, with the endocardium and epicardium layers as the inner-most and outer-most regions, respectively. However, because the distance between the epicardium and the non-contractile pericardium is small, and because the pericardium layer has high image intensities, non-expert users and automatic segmentation algorithms may erroneously include the pericardium in the region of interest. Since the pericardium is bright but does not contain contractile muscle, the inclusion of the pericardium may result in an underestimation of both global and regional strain values. When enough non-contractile pericardium is included, even a healthy region may be identified as infarcted due to the low strain values indicating impaired heart motion. As a result, additional time and effort may be spent trying to diagnose the patient.

Figure 1:
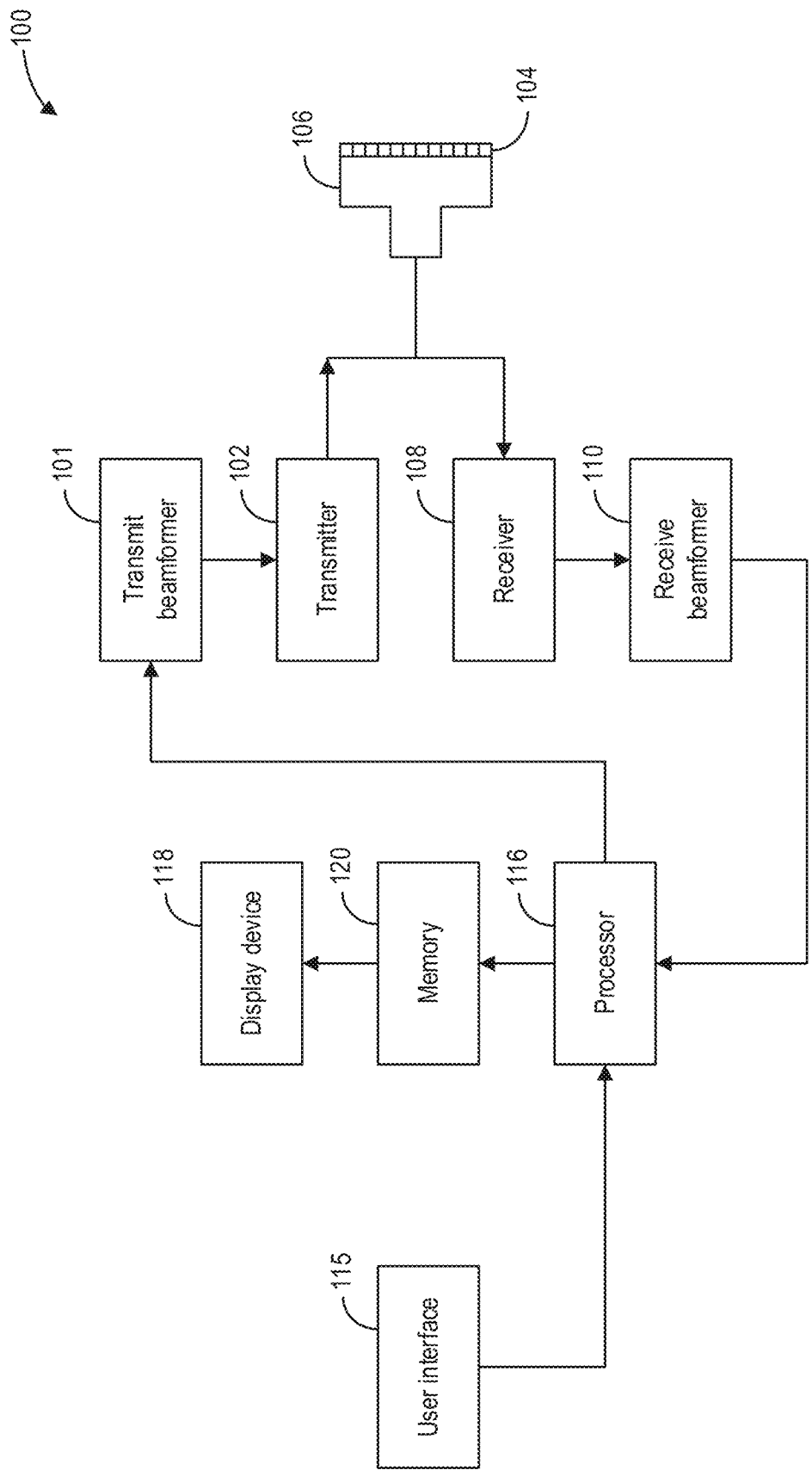
FIG. 1 shows a block schematic diagram of an ultrasound imaging system, according to an embodiment.
Figure 2:
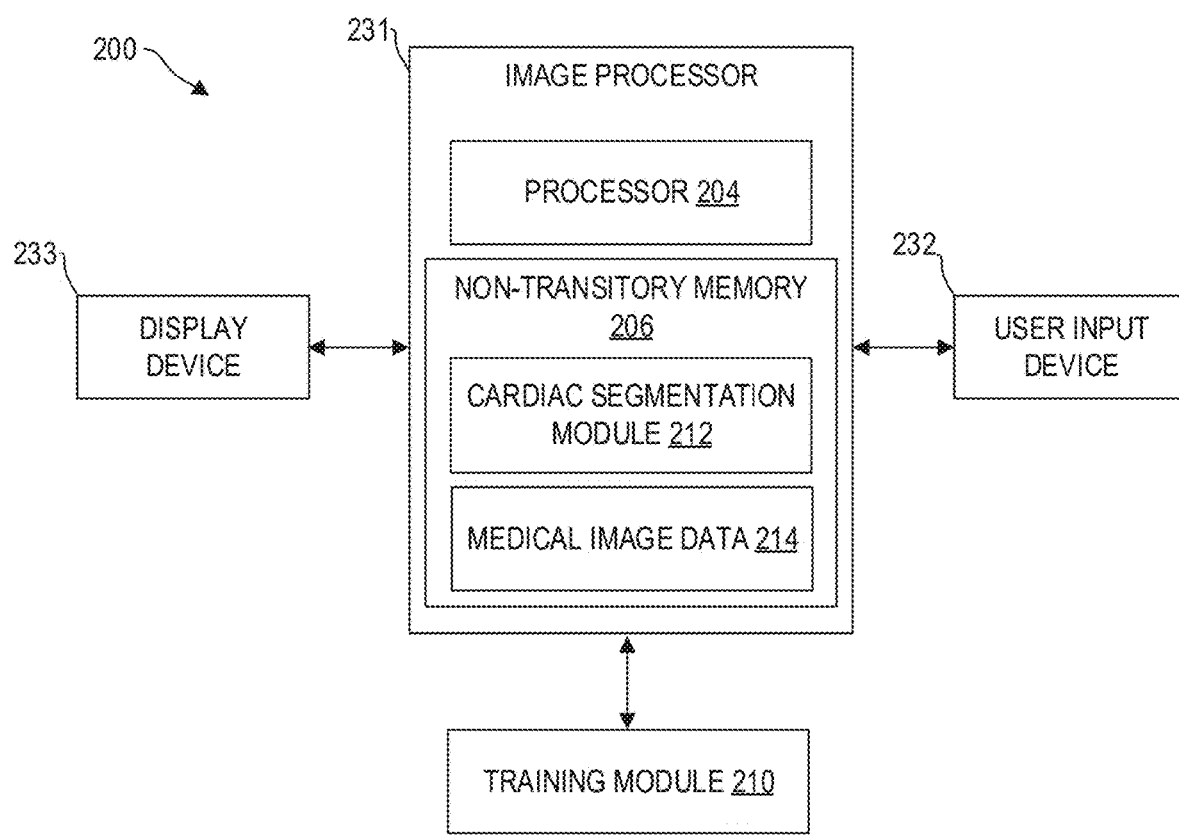
FIG. 2 is a schematic diagram illustrating an image processing system for segmenting myocardium in ultrasound images, according to embodiment.
Figure 7:
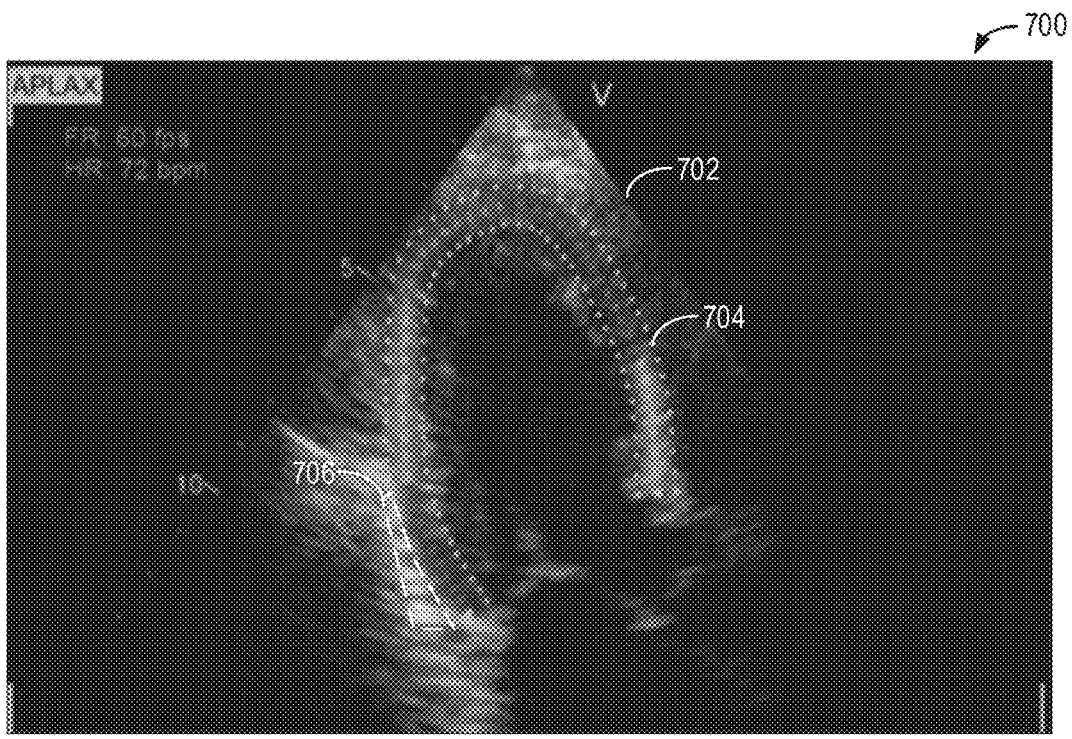
FIG. 7 shows a first example display output showing a selected myocardium region of interest relative to a pericardium region, according to an embodiment.
Figure 8:
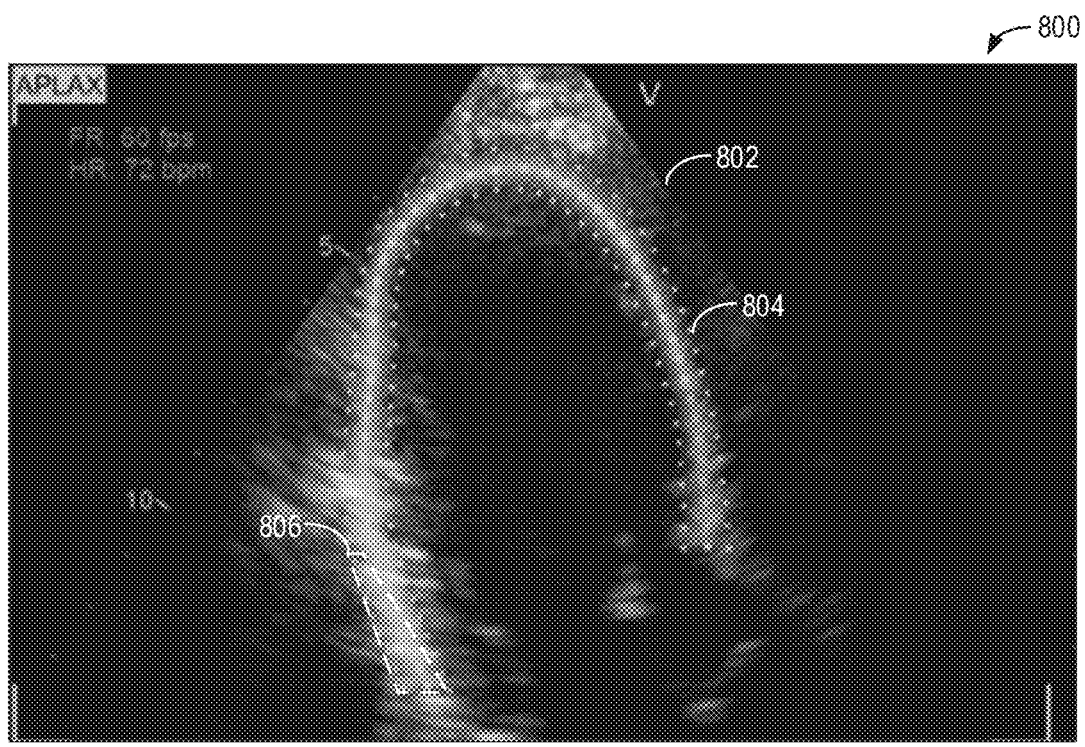
FIG. 8 shows a second example display output showing a selected myocardium region of interest relative to a pericardium region, according to an embodiment.
Figure 9:
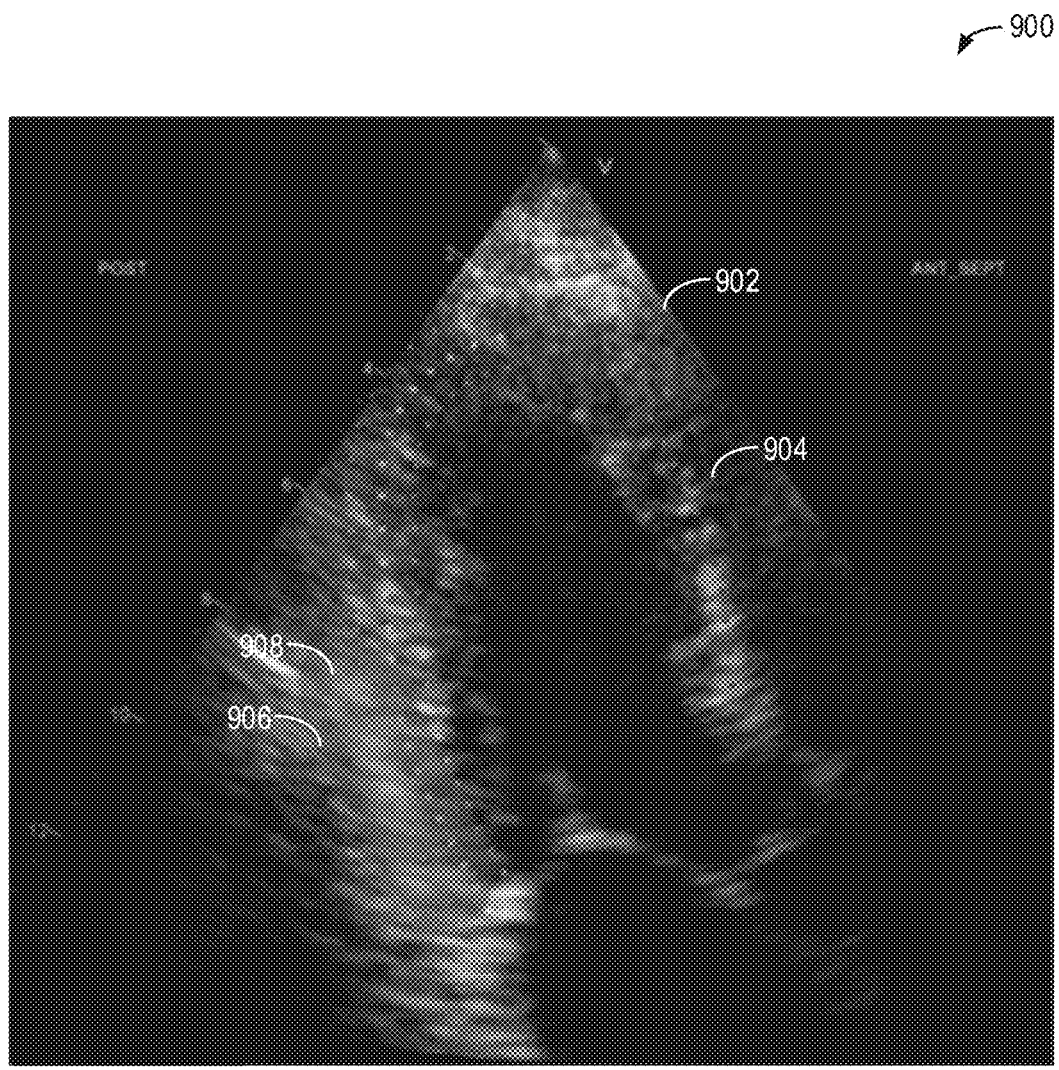
FIG. 9 shows a third example display output showing a selected myocardium region of interest relative to a pericardium region having an overlaid pericardium mask, according to an embodiment.
Figure 10:
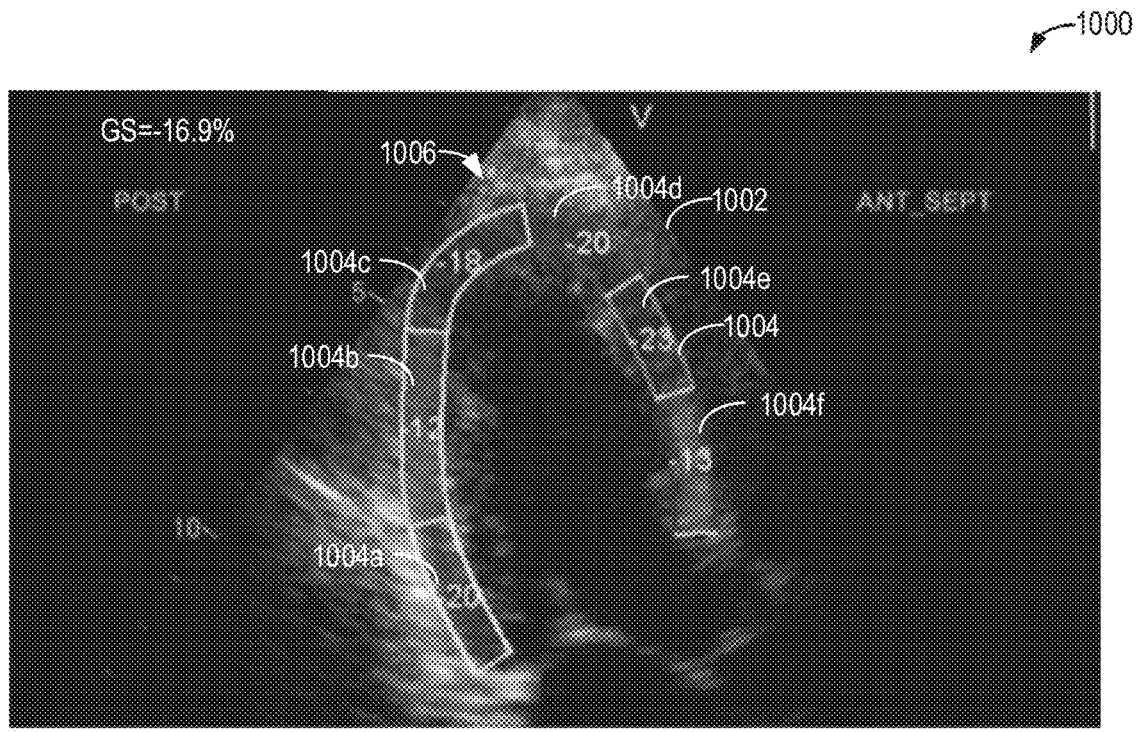
FIG. 10 shows exemplary output of cardiac strain values wherein the pericardium has been excluded, according to an embodiment.
Figure 11:
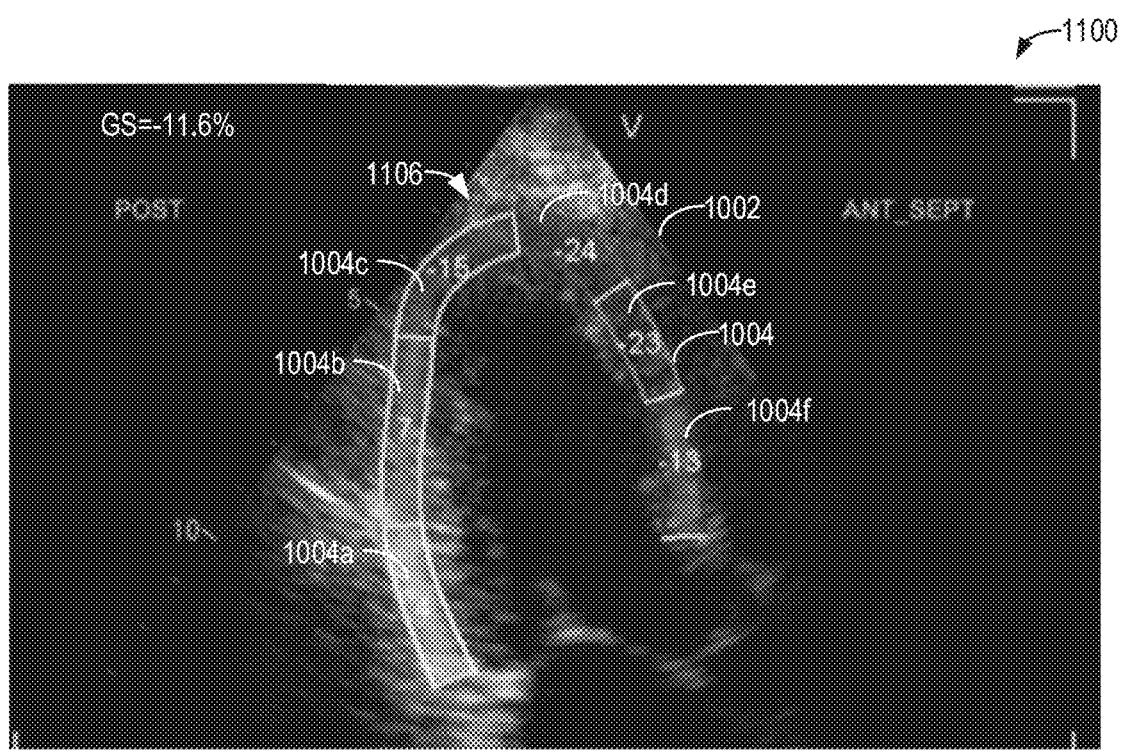
FIG. 11 shows exemplary output of cardiac strain values wherein the pericardium has not been excluded, according to an embodiment.

Thus, according to embodiments described herein, images of the heart may be acquired by an ultrasound imaging system, such as the ultrasound imaging system shown in FIG. 1. An example image processing system that may be used to segment pericardium and/or myocardium is shown in FIG. 2. For example, the image processing may employ image processing and deep learning algorithms to segment and mask the pericardium within the ultrasound images before the ultrasound images and the mask are fed into a speckle tracking algorithm, such as according to the workflow schematically shown in FIG. 3 and according to the method of FIG. 4. In some embodiments, a user may manually define the region of interest, and the region of interest, with the pericardium mask excluded, may be analyzed to determine strain values, such as according to the method of FIG. 5. In other embodiments, the image processing system may further employ image processing and deep learning algorithms to segment the myocardium to define the region of interest for strain calculations, such as according to the method of FIG. 6. Examples of the region of interest are shown in FIGS. 7 and 8. For example, FIG. 7 shows a more accurate placement of the region of interest that does not overlap with a pericardium region, whereas FIG. 8 shows a less accurate placement of the region of interest that overlaps with the pericardium. An example of the pericardium mask overlaid on an ultrasound image to exclude the pericardium from the region of interest is shown in FIG. 9. FIGS. 10 and 11 show example strain value outputs (e.g., strain maps), including outputs when the pericardium is masked and thereby excluded (FIG. 10) and corresponding outputs when the pericardium is not masked and excluded (FIG. 11).

Advantages that may be realized in the practice of some embodiments of the described systems and techniques are that areas of healthy function and areas of impaired muscle function may be more easily identified. For example, more accurate strain value calculations may make it easier for a clinician to distinguish healthy regions that experience strong contraction, and thus more strain, from regions having impaired contraction, and thus less strain. In contrast, underestimating the strain values by including the pericardium may obscure the actual regions of impaired muscle function by showing larger areas of impaired function even in healthy tissue. Further, the systems and techniques described herein may reduce variability between users and between exams, as any pericardium erroneously included in the region of interest by the user may not be included in the strain value calculations. Overall, more accurate and timely diagnoses may be obtained.

Although the systems and methods described below for evaluating medical images are discussed with reference to an ultrasound imaging system, it may be noted that the methods described herein may be applied to a plurality of imaging systems. As the processes described herein may be applied to pre-processed imaging data and/or to processed images, the term "image" is generally used throughout the disclosure to denote both pre-processed and partially-processed image data (e.g., pre-beamformed radio frequency or in-phase/quadrature data, pre-scan converted radio frequency data) as well as fully processed images (e.g., scan converted and filtered images ready for display).

Referring to FIG. 1, a schematic diagram of an ultrasound imaging system 100 in accordance with an embodiment of the disclosure is shown. However, it may be understood that embodiments set forth herein may be implemented using other types of medical imaging modalities (e.g., magnetic resonance imaging, computed tomography, positron emission tomography, and so on). The ultrasound imaging system 100 includes a transmit beamformer 101 and a transmitter 102 that drives elements (e.g., transducer elements) 104 within a transducer array, herein referred to as a probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. The transducer elements 104 may be comprised of a piezoelectric material. When a voltage is applied to the piezoelectric material, the piezoelectric material physically expands and contracts, emitting an ultrasonic spherical wave. In this way, the transducer elements 104 may convert electronic transmit signals into acoustic transmit beams.

After the transducer elements 104 of the probe 106 emit pulsed ultrasonic signals into the body (of a patient), the pulsed ultrasonic signals are back-scattered from structures within an interior of the body, like blood cells and muscular tissue, to produce echoes that return to the elements 104. The echoes are converted into electrical signals, or ultrasound data, by the elements 104, and the electrical signals are received by a receiver 108. The electrical signals representing the received echoes are passed through a receive beamformer 110 that performs beamforming and outputs ultrasound data, which may be in the form of a radiofrequency (RF) signal. Additionally, the transducer elements 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be positioned within the probe 106. The terms "scan" or "scanning" may also be used in this disclosure to refer to acquiring data through the process of transmitting and receiving ultrasonic signals. The term "data" may be used in this disclosure to refer to one or more datasets acquired with an ultrasound imaging system. In one embodiment, data acquired via the ultrasound imaging system 100 may be processed via an imaging processing system, as will be elaborated below with respect to FIG. 2.

A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of a rotary element, a mouse, a keyboard, a trackball, hard keys linked to specific actions, soft keys that may be configured to control different functions, and a graphical user interface displayed on a display device 118. In some embodiments, the display device 118 may include a touch-sensitive display, and thus, the display device 118 may be included in the user interface 115. In some embodiments, the user interface 115 may further include an audio system, such as one or more speakers, to output sound.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. As used herein, the term "electronic communication" may be defined to include both wired and wireless communications. The processor 116 may control the probe 106 to acquire data according to instructions stored on a memory of the processor and/or a memory 120. As one example, the processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processing unit (CPU), according to an embodiment. According to other embodiments, the processor 116 may include other electronic components capable of carrying out processing functions, such as a digital signal processor, a field-programmable gate array (FPGA), or a graphics board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphics board. According to another embodiment, the processor 116 may also include a complex demodulator (not shown) that demodulates RF data and generates raw data. In another embodiment, the demodulation may be carried out earlier in the processing chain.

The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay (e.g., substantially at the time of occurrence). For example, an embodiment may acquire images at a real-time rate of 7-20 frames/sec. The ultrasound imaging system 100 may acquire two-dimensional (2D) data of one or more planes at a significantly faster rate. However, it should be understood that the real-time frame-rate may be dependent on a length (e.g., duration) of time that it takes to acquire and/or process each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec.

In some embodiments, the data may be stored temporarily in a buffer (not shown) during a scanning session and processed in less than real-time in a live or off-line operation. Some embodiments of the disclosure may include multiple processors (not shown) to handle the processing tasks that are handled by the processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hertz (Hz) to 30 Hz (e.g., 10 to 30 frames per second). Images generated from the data may be refreshed at a similar frame-rate on the display device 118. Other embodiments may acquire and display data at different rates. For example, some embodiments may acquire data at a frame-rate of less than 10 Hz or greater than 30 Hz depending on the size of the frame and the intended application. The memory 120 may store processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present disclosure, data may be processed in different mode-related modules by the processor 116 (e.g., B-mode, Color Doppler, M-mode, Color M-mode, spectral Doppler, elastography, tissue velocity imaging, strain, strain rate, and the like) to form 2D or three-dimensional (3D) images. When multiple images are obtained, the processor 116 may also be configured to stabilize or register the images. For example, one or more modules may generate B-mode, color Doppler, M-mode, color M-mode, color flow imaging, spectral Doppler, elastography, tissue velocity imaging (TVI), strain (e.g., speckle tracking echocardiography), strain rate, and the like, and combinations thereof. As one example, the one or more modules may process B-mode data, which may include 2D or 3D B-mode data, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image loop (e.g., cine loop) in real-time while a procedure (e.g., ultrasound imaging) is being performed on the patient. The video processor module may include a separate image memory, and the ultrasound images may be written to the image memory in order to be read and displayed by the display device 118.

Further, the components of the ultrasound imaging system 100 may be coupled to one another to form a single structure, may be separate but located within a common room, or may be remotely located with respect to one another. For example, one or more of the modules described herein may operate in a data server that has a distinct and remote location with respect to other components of the ultrasound imaging system 100, such as the probe 106 and the user interface 115. Optionally, the ultrasound imaging system 100 may be a unitary system that is capable of being moved (e.g., portably) from room to room. For example, the ultrasound imaging system 100 may include wheels or may be transported on a cart, or may comprise a handheld device.

For example, in various embodiments of the present disclosure, one or more components of the ultrasound imaging system 100 may be included in a portable, handheld ultrasound imaging device. For example, the display device 118 and the user interface 115 may be integrated into an exterior surface of the handheld ultrasound imaging device, which may further contain the processor 116 and the memory 120 therein. The probe 106 may comprise a handheld probe in electronic communication with the handheld ultrasound imaging device to collect raw ultrasound data. The transmit beamformer 101, the transmitter 102, the receiver 108, and the receive beamformer 110 may be included in the same or different portions of the ultrasound imaging system 100. For example, the transmit beamformer 101, the transmitter 102, the receiver 108, and the receive beamformer 110 may be included in the handheld ultrasound imaging device, the probe, and combinations thereof.

Referring now to FIG. 2, an example medical image processing system 200 is shown. In some embodiments, the medical image processing system 200 is incorporated into a medical imaging system, such as an ultrasound imaging system (e.g., the ultrasound imaging system 100 of FIG. 1), a magnetic resonance imaging (MRI) system, a computed tomography (CT) system, a single-photon emission computed tomography (SPECT) system, and the like. In some embodiments, at least a portion of the medical image processing system 200 is disposed at a device (e.g., an edge device or server) communicably coupled to the medical imaging system via wired and/or wireless connections. In some embodiments, the medical image processing system 200 is disposed at a separate device (e.g., a workstation) that can receive images from the medical imaging system or from a storage device that stores the images generated by the medical imaging system. The medical image processing system 200 may comprise an image processor 231, a user input device 232, and a display device 233. For example, the image processor 231 may be operatively/communicatively coupled to the user input device 232 and the display device 233.

The image processor 231 includes a processor 204 configured to execute machine readable instructions stored in a non-transitory memory 206. The processor 204 may be single core or multi-core, and the programs executed by the processor 204 may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration. In some embodiments, the processor 204 may include other electronic components capable of carrying out processing functions, such as a digital signal processor, a FPGA, or a graphics board. In some embodiments, the processor 204 may include multiple electronic components capable of carrying out processing functions. For example, the processor 204 may include two or more electronic components selected from a plurality of possible electronic components, including a central processor, a digital signal processor, a field-programmable gate array, and a graphics board. In still further embodiments, the processor 204 may be configured as a graphical processing unit (GPU), including parallel computing architecture and parallel processing capabilities.

In the embodiment shown in FIG. 2, the non-transitory memory 206 stores a cardiac segmentation module 212 and medical image data 214. The cardiac segmentation module 212 includes one or more algorithms, including machine learning models, to process input medical images from the medical image data 214. Specifically, the cardiac segmentation module 212 may provide an artificial intelligence system for identifying and segmenting pericardium within the medical image data 214. For example, the cardiac segmentation module 212 may include one or more deep learning networks comprising a plurality of weights and biases, activation functions, loss functions, gradient descent algorithms, and instructions for implementing the one or more deep learning networks to process the input medical images. Additionally or alternatively, the cardiac segmentation module 212 may store instructions for implementing a neural network, such as a convolutional neural network, for identifying pericardium captured in the medical image data 214. The cardiac segmentation module 212 may include trained and/or untrained neural networks and may further include training routines, or parameters (e.g., weights and biases), associated with one or more neural network models stored therein. Additionally or alternatively, the cardiac segmentation module 212 may include image recognition algorithms, shape or edge detection algorithms, and the like for identifying the pericardium. The cardiac segmentation module 212 may further generate a mask of the pericardium. For example, the mask of the pericardium may be the output of the cardiac segmentation module 212. In some embodiments, the cardiac segmentation module 212 may evaluate the medical image data 214 as it is acquired in real-time. Additionally or alternatively, the cardiac segmentation module 212 may evaluate the medical image data 214 offline, not in real-time.

In some embodiments, the cardiac segmentation module 212 may further include trained and/or untrained neural networks for identifying and segmenting myocardium (e.g., cardiac muscle) in the medical image data 214 in addition to trained and/or untrained neural networks for identify and segmenting the pericardium. Additionally or alternatively, separate cardiac segmentation modules may be included within, or may be accessed by, the image processor 231. For example, the image processor 231 may use a first cardiac segmentation module to mask the pericardium and use a second cardiac segmentation module, separate from the first, to select (e.g., identify and segment) a region of interest comprising the myocardium.

The image processor 231 may be communicatively coupled to a training module 210, which includes instructions for training one or more of the machine learning models stored in the cardiac segmentation module 212. The training module 210 may include instructions that, when executed by a processor, cause the processor to build a model (e.g., a mathematical model) based on sample data to make predictions or decisions regarding the segmentation of tissues within the heart without the explicit programming of a conventional algorithm that does not utilize machine learning. In one example, the training module 210 includes instructions for receiving training data sets from the medical image data 214. The training data sets comprise sets of medical images (e.g., B-mode cardiac ultrasound images), associated ground truth labels/images, and associated model outputs (e.g., a mask of the pericardium) for use in training one or more of the machine learning models stored in the cardiac segmentation module 212. The training module 210 may receive medical images, associated ground truth labels/images, and associated model outputs for use in training the one or more machine learning models from sources other than the medical image data 214, such as other image processing systems, the cloud, etc. In some embodiments, one or more aspects of the training module 210 may include remotely accessible networked storage devices configured in a cloud computing configuration.

In some embodiments, the training module 210 is included in the non-transitory memory 206. Additionally or alternatively, in some embodiments, the training module 210 may be used to generate the cardiac segmentation module 212 offline and remote from the medical image processing system 200. In such embodiments, the training module 210 may not be included in the medical image processing system 200 but may generate data stored in the medical image processing system 200. For example, the cardiac segmentation module 212 may be pre-trained with the training module 210 at a place of manufacture.

The non-transitory memory 206 further stores the medical image data 214. The medical image data 214 may include, for example, functional and/or anatomical images captured by an imaging modality, such as ultrasound imaging systems, MRI systems, CT systems, and so forth. As one example, the medical image data 214 may include ultrasound images, such as cardiac ultrasound images. Further, the medical image data 214 may include one or more of 2D images, 3D images, static single frame images, and multi-frame cine-loops (e.g., movies).

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices in a cloud computing configuration. As one example, the non-transitory memory 206 may be part of a picture archiving and communication system (PACS) that is configured to store patient medical histories (e.g., electronic medical records), imaging data, test results, diagnosis information, management information, and/or scheduling information, for example.

The medical image processing system 200 may further include the user input device 232. The user input device 232 may comprise one or more of a touchscreen, a keyboard, a mouse, a trackpad, a motion sensing camera, or other device configured to enable a user to interact with and manipulate data stored within the image processor 231. As an example, the user input device 232 may enable a user to select images for analysis by the cardiac segmentation module 212.

The display device 233 may include one or more display devices utilizing any type of display technology. In some embodiments, the display device 233 may comprise a computer monitor and may display unprocessed images, processed images, parametric maps, and/or exam reports. The display device 233 may be combined with the processor 204, the non-transitory memory 206, and/or the user input device 232 in a shared enclosure or may be a peripheral display device. The display device 233 may include a monitor, a touchscreen, a projector, or another type of display device, which may enable a user to view medical images and/or interact with various data stored in the non-transitory memory 206. In some embodiments, the display device 233 may be included in a mobile device, such as a smartphone, a tablet, a smartwatch, or the like.

It may be understood that the medical image processing system 200 shown in FIG. 2 is one non-limiting embodiment of an image processing system, and other imaging processing systems may include more, fewer, or different components without departing from the scope of this disclosure. Further, in some embodiments, at least portions of the medical image processing system 200 may be included in the ultrasound imaging system 100 of FIG. 1, or vice versa (e.g., at least portions of the ultrasound imaging system 100 may be included in the medical image processing system 200).

As used herein, the terms "system" and "module" may include a hardware and/or software system that operates to perform one or more functions. For example, a module or system may include or may be included in a computer processor, controller, or other logic-based device that performs operations based on instructions stored on a tangible and non-transitory computer readable storage medium, such as a computer memory. Alternatively, a module or system may include a hard-wired device that performs operations based on hard-wired logic of the device. Various modules or systems shown in the attached figures may represent the hardware that operates based on software or hardwired instructions, the software that directs hardware to perform the operations, or a combination thereof.

"Systems" or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 3:
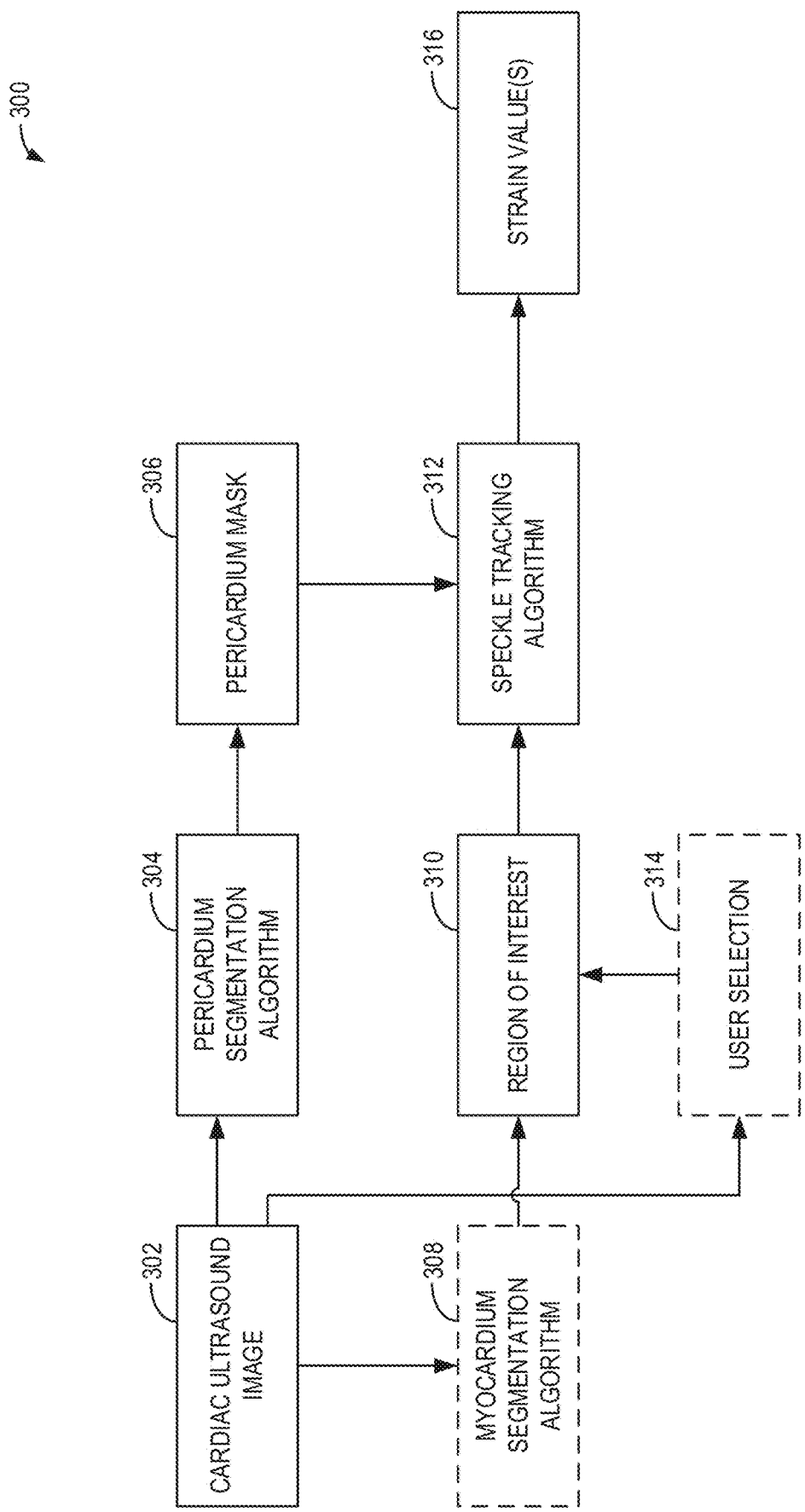
FIG. 3 shows a block schematic diagram of a workflow for performing strain calculations from cardiac ultrasound images with pericardium masking and exclusion.

FIG. 3 shows an example workflow 300 for excluding the pericardium from strain value calculations performed on cardiac ultrasound images. In one embodiments, the workflow 300 is performed by the medical image processing system 200 of FIG. 2. The workflow 300 provides a high-level overview of a pericardium masking and strain value calculation process that will be further described below with respect to FIGS. 4-6. A cardiac ultrasound image 302 is input into a pericardium segmentation algorithm 304. The pericardium segmentation algorithm 304 may use one or more machine learning-based and/or programmed algorithms to identify and segment the pericardium in the cardiac ultrasound image 302, such as described above with respect to the cardiac segmentation module 212 of FIG. 2. The pericardium segmentation algorithm 304 outputs a pericardium mask 306 corresponding to regions of the cardiac ultrasound image 302 having the identified and segmented pericardium.

The cardiac ultrasound image 302 is optionally input into a myocardium segmentation algorithm 308. The myocardium segmentation algorithm 308 may use one or more machine learning-based and/or programmed algorithms to identify and segment the myocardium in the cardiac ultrasound image 302. The myocardium segmentation algorithm may output a region of interest 310 corresponding to the identified and segmented myocardium, which may be input into a speckle tracking algorithm 312 along with the pericardium mask 306. Alternatively, a user selection 314 may generate the region of interest 310 from the cardiac ultrasound image 302. For example, the user selection 314 may be received via a user input device, such as the user input device 232 of FIG. 2. In some embodiments, the myocardium segmentation algorithm 308 may output the region of interest 310, which may be refined by the user selection 314 before it is input into the speckle tracking algorithm 312. In other embodiments, the myocardium segmentation algorithm 308 may refine the region of interest 310 generated from the user selection 314 before it is input into the speckle tracking algorithm 312. Thus, the region of interest 310 may be generated via one or a combination of the myocardium segmentation algorithm 308 and the user selection 314.

It may be understood that although the workflow 300 shown in FIG. 3 includes the pericardium segmentation algorithm 304, the myocardium segmentation algorithm 308, and the speckle tracking algorithm 312 as separate processes, in other embodiments, one or both of the pericardium segmentation algorithm 304 and the myocardium segmentation algorithm 308 may be combined with the speckle tracking algorithm 312. For example, the speckle tracking algorithm 312 may be adapted to identify and exclude the pericardium from the region of interest 310. Additionally or alternatively, the speckle tracking algorithm 312 may be adapted to select the region of interest 310 corresponding to the myocardium directly from the cardiac ultrasound image 302.

The speckle tracking algorithm 312 receives (or generates, in alternative embodiments) the pericardium mask 306 and the region of interest 310 and outputs one or more strain values 316. The one or more strain values 316 may include longitudinal, circumferential, and radial strain values for different portions of the region of interest corresponding to different anatomical regions, for example. It may be understood that the speckle tracking algorithm 312 may receive pericardium masks and regions of interest for a plurality of cardiac ultrasound images in addition to the cardiac ultrasound image 302 in order to calculate the one or more strain values 316.

Figure 4:
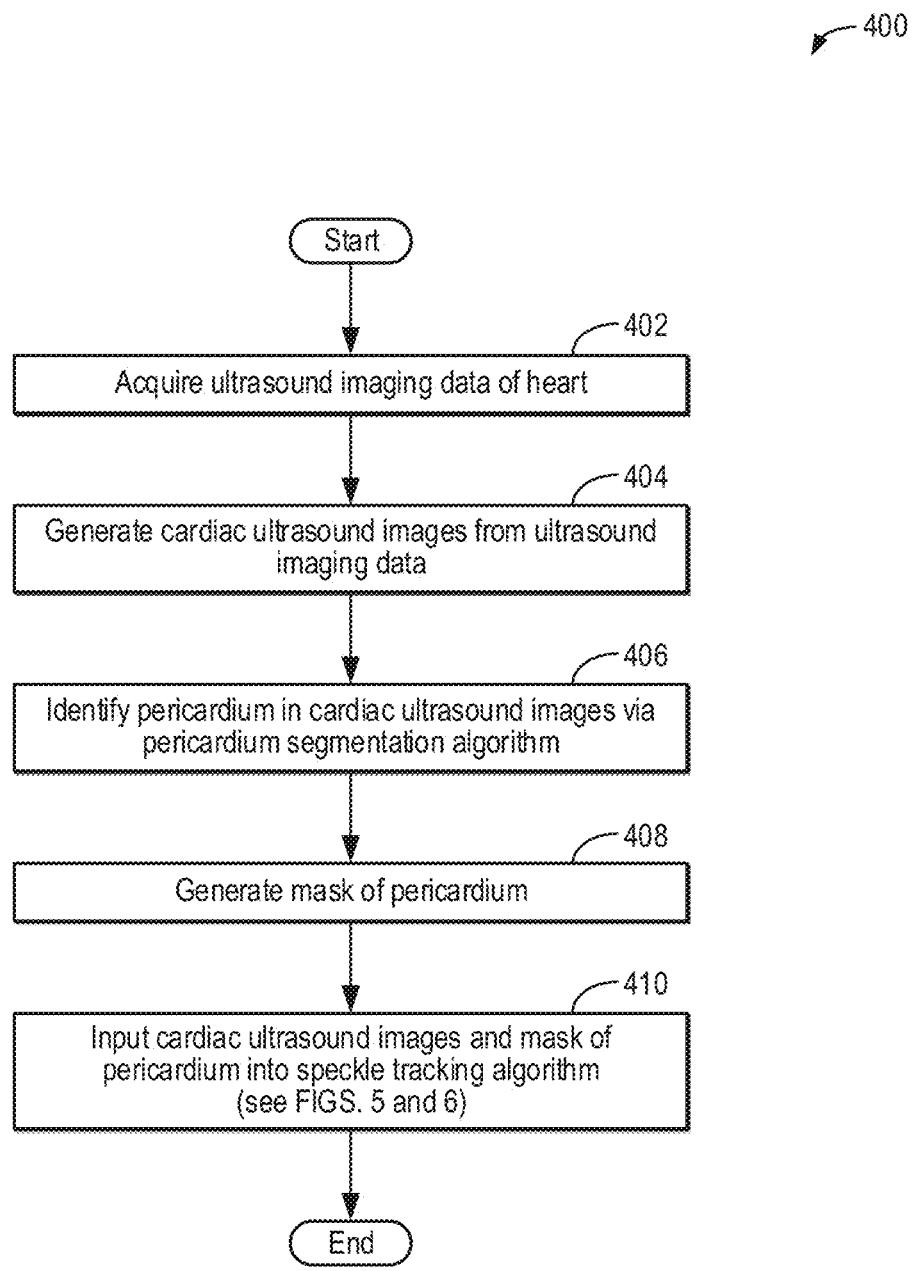
FIG. 4 shows a flow chart of an example method for identifying and masking pericardium in a cardiac ultrasound image, according to an embodiment.

Turning now to FIG. 4, an example method 400 is provided for identifying and masking pericardium in cardiac ultrasound images. The method 400 will be described for ultrasound images acquired using the ultrasound imaging system 100 of FIG. 1, although other ultrasound imaging systems may be used. Further, the method 400 may be adapted to other imaging modalities. The method 400 and the rest of the methods included herein may be implemented by one or more of the above described systems, including the ultrasound imaging system 100 of FIG. 1 and the medical image processing system 200 of FIG. 2. As such, the method 400 may be stored as executable instructions in non-transitory memory, such as the memory 120 of FIG. 1 and/or the non-transitory memory 206 of FIG. 2, and executed by a processor, such as the processor 116 of FIG. 1 and/or the processor 204 of FIG. 2. Further, in some embodiments, the method 400 is performed in real-time, as the cardiac ultrasound images are acquired, while in other embodiments, at least portions of the method 400 are performed offline, after the cardiac ultrasound images are acquired (e.g., following termination of a scan of a subject via the ultrasound imaging system, where, during the scan, a probe of the ultrasound imaging system may be energized to acquire cardiac ultrasound images of the subject, and following termination of the scan, the probe may not be energized to acquire cardiac ultrasound images). For example, the processor may evaluate cardiac ultrasound images that are stored in memory even while the ultrasound system is not actively being operated to acquire images. Further still, at least parts of the method 400 may be performed in parallel. For example, ultrasound data for a second image may be acquired while a first cardiac ultrasound image is generated, ultrasound data for a third image may be acquired while the second cardiac ultrasound image is generated, and so on.

At 402, the method 400 includes acquiring ultrasound imaging data of the heart. The ultrasound imaging data may be acquired according to an ultrasound protocol, which may be selected by an operator (e.g., user) of the ultrasound imaging system via a user interface (e.g., the user interface 115 of FIG. 1). As one example, the operator may select the ultrasound protocol from a plurality of possible ultrasound protocols using a drop-down menu or by selecting a virtual button. Alternatively, the system may automatically select the protocol based on data received from an electronic medical record (EMR) associated with the patient. For example, the EMR may include previously performed exams, diagnoses, and current treatments, which may be used to select the ultrasound protocol. Further, in some examples, the operator may manually input and/or update parameters to use for the ultrasound protocol. The ultrasound protocol may be a system guided protocol, where the system guides the operator through the protocol step-by-step, or a user guided protocol, where the operator follows a lab-defined or self-defined protocol without the system enforcing a specific protocol or having prior knowledge of the protocol steps.

Further, the ultrasound protocol may include a plurality of views and/or imaging modes that are sequentially performed. Using cardiac ultrasound imaging as an example, the ultrasound protocol may include a four-chamber view of the left ventricle with B-mode and a four-chamber view focused on the right ventricle with B-mode. Additionally or alternatively, the ultrasound protocol may include an apical long-axis (APLAX) view of the heart. It may be understood that in some examples, a partial view of the heart may be acquired, such as a two-chamber view of the left ventricle and left atrium or a single chamber view (e.g., only the left ventricle). In some examples, additional imaging modes may be used, such as color flow imaging (CFI). Further, the ultrasound protocol may specify a frame-rate for acquiring the ultrasound imaging data. The frame-rate for the acquisition may be increased when a regional, partial view of the heart is acquired compared with a full acquisition because a field of view is smaller. In some examples, a plurality of regional views of the heart may be acquired, with each of the plurality of regional views obtaining a different partial view of the heart, in order to obtain a more accurate mapping of strain values in each region.

The ultrasound imaging data may be acquired with an ultrasound probe by transmitting and receiving ultrasonic signals according to the ultrasound protocol. In the above cardiac ultrasound imaging example, performing the ultrasound protocol includes acquiring ultrasound data for some or all of the above-mentioned views and imaging modes. Acquiring the ultrasound data according to the ultrasound protocol may include the system displaying instructions on the user interface and/or display, for example, to guide the operator through the acquisition of the designated views. Additionally or alternatively, the ultrasound protocol may include instructions for the ultrasound system to automatically acquire some or all of the data or perform other functions. For example, the ultrasound protocol may include instructions for the user to move, rotate and/or tilt the ultrasound probe, as well as to automatically initiate and/or terminate a scanning process and/or adjust imaging parameters of the ultrasound probe, such as ultrasound signal transmission parameters, ultrasound signal receive parameters, ultrasound signal processing parameters, or display parameters. Further, the acquired ultrasound data may include one or more image parameters calculated for each pixel or group of pixels (for example, a group of pixels assigned the same parameter value) to be displayed, where the one or more calculated image parameters include, for example, one or more of an intensity, texture, graininess, contractility, deformation, and rate of deformation value.

At 404, the method 400 includes generating cardiac ultrasound images from the acquired ultrasound imaging data. The cardiac ultrasound images may also be referred to herein as ultrasound images of the heart. At least one cardiac ultrasound image may be generated for each view of the ultrasound protocol. For example, the signal data acquired during the method at 402 is processed and analyzed by the processor in order to produce an ultrasound image. The processor may include an image processing module that receives the signal data (e.g., imaging data) acquired at 402 and processes the received imaging data. For example, the image processing module may process the ultrasound signals to generate slices or frames of ultrasound information (e.g., ultrasound images) for displaying to the operator. In one example, generating the image may include determining an intensity value for each pixel to be displayed based on the received imaging data (e.g., 2D or 3D ultrasound data). As such, the generated cardiac ultrasound images may be 2D or 3D depending on the mode of ultrasound being used (e.g., CFI, acoustic radiation force imaging, B-mode, A-mode, M-mode, spectral Doppler, acoustic streaming, tissue Doppler module, C-scan, or elastography). The present example will be discussed for 2D B-mode cardiac ultrasound images, although it may be understood that any of the above mentioned modes or other imaging modes may be used according to the selected ultrasound protocol.

At 406, the method 400 includes identifying the pericardium in the cardiac ultrasound images via a pericardium segmentation algorithm. For example, each cardiac ultrasound image may be input into the pericardium segmentation algorithm in substantially real-time, as each ultrasound image is generated from real-time ultrasound imaging data. Alternatively, each cardiac ultrasound image may be processed by the pericardium segmentation algorithm offline, after the ultrasound imaging data acquisition is finished. In some embodiments, the pericardium segmentation algorithm may be included in a cardiac segmentation module, such as the cardiac segmentation module 212 described above with respect to FIG. 2. The pericardium segmentation algorithm may include one or more image recognition algorithms, shape detection algorithms, and/or edge detection algorithms for distinguishing the pericardium from the myocardium and other tissues and/or structures of the heart. The pericardium segmentation algorithm may further include one or more machine learning algorithms and/or traditionally programmed algorithms for identifying and segmenting the pericardium. For example, the pericardium may be identifiable based on its relative positioning in the ultrasound images and pixel contrast between the brighter (e.g., higher intensity) pixels of the pericardium compared with the dimmer (e.g., lower intensity) pixels of the neighboring myocardium. Further, because the pericardium is non-contractile, its length may not change over time. As such, the pericardium may be further identifiable by the pericardium segmentation algorithm based on its relatively unchanging physical dimensions from image frame to image frame.

At 408, the method 400 includes generating a mask of the pericardium. The mask may define one or more regions of pixels in a corresponding cardiac ultrasound image where the pericardium has been identified. For example, the mask may be a binary image wherein pixel values in the region(s) where the pericardium has been identified are set to zero and the pixel values in all other areas that do not include the pericardium are set to one. The mask of the pericardium includes a defined shape and a defined positional location on the corresponding ultrasound image. In some embodiments, all of the images generated for a particular view of the ultrasound protocol may use a same mask. For example, a single mask may be generated from a representative image of the particular view.

In some examples, the mask may be visually represented in relation to unmasked pixels of the cardiac ultrasound images by one or more overlays shown by a display device displaying the cardiac ultrasound images. For example, the cardiac ultrasound images may be displayed at the display device (e.g., monitor) for analysis (e.g., diagnosis of the imaged subject, etc.) by the operator of the ultrasound imaging system (e.g., a technician). The pixels included in the mask may be represented by a darkened overlay, as one example, where the pixels included in the mask are dimmed relative to the pixels not included by the mask. In some examples, the overlay may have a color or other appearance to visually distinguish the pixels included in the mask from surrounding pixels (e.g., pixels included in the myocardium region of interest). In another example, the pixels included in the mask may be enclosed within a boundary line visually defining the bounds of the mask within the cardiac ultrasound images. In yet other examples, one or more image processing protocols (e.g., Gaussian blur) may be applied to the visual representation of the mask to further distinguish the pixels included in the mask from the pixels not included in the mask.

At 410, the method 400 includes inputting the cardiac ultrasound images and mask of the pericardium into a speckle tracking algorithm, as will be elaborated below with respect to FIGS. 5 and 6. For example, when the mask is applied to the corresponding cardiac ultrasound image, the pixels within the mask may be hidden (e.g., reversibly set to zero) while the pixels outside of the mask (e.g., where the pixel values are set to one in the binary image) remain unchanged. Further, the mask hides the region within the mask in a non-destructive manner in that the pixel values in the masked region in the corresponding ultrasound image are not deleted. For example, the pixel values may be restored by removing the mask (e.g., unmasking the cardiac ultrasound image). As such, the corresponding cardiac ultrasound image remains unaltered by the masking process, while the masked region is excluded from evaluation by the speckle tracking algorithm. The method 400 may then end.

Figure 5:
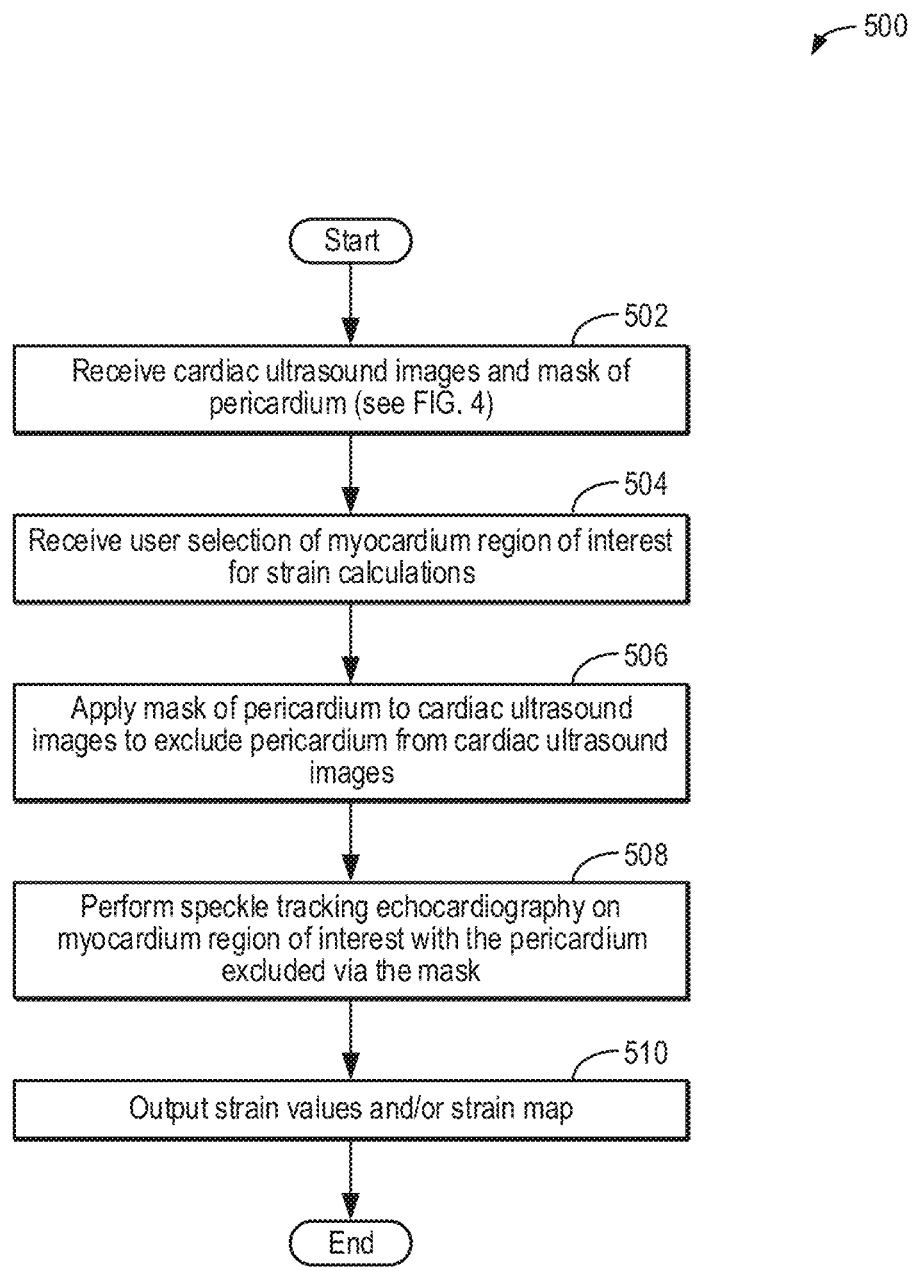
FIG. 5 shows a flow chart of an example method for calculating cardiac strain values by excluding regions within a generated pericardium mask, according to an embodiment.

Continuing to FIG. 5, an example method 500 for calculating cardiac strain values while excluding regions within a generated pericardium mask is shown. The method 500 provides a first embodiment of performing the strain value calculations. In some embodiments, the method 500 may be performed as a part of the method 400 of FIG. 4 (e.g., at 410). In other embodiments, the method 500 may be executed separately and use cardiac ultrasound images and a mask of the pericardium generated by another method, such as the method 400 of FIG. 4. In some embodiments, the method 500 may be executed in response to an operator request for a strain analysis.

At 502, the method 500 includes receiving cardiac ultrasound images and the mask of the pericardium, such as generated via the method 400 of FIG. 4. In some embodiments, the cardiac ultrasound images and the mask of the pericardium may be received in real-time, as the cardiac ultrasound images and the mask of the pericardium are generated. In other embodiments, the cardiac ultrasound images may be stored in memory before being analyzed. For example, the cardiac ultrasound images may be stored in a memory for a duration of time (e.g., minutes, hours, days) before the pericardium mask is generated, and after the pericardium mask is generated, the cardiac ultrasound images may be further stored for another duration of time before being further evaluated to determine the strain values or evaluated once the pericardium mask is generated. In another example, the pericardium mask may be generated at substantially the same time as the cardiac ultrasound images are generated, and the pericardium mask may be stored in the memory along with the cardiac ultrasound images before being accessed by the method 500. Thus, the method 500 may be performed in real-time with the method 400 of FIG. 4 or may be performed using cardiac ultrasound images and an associated pericardium mask generated previously.

At 504, the method 500 includes receiving a user selection of a myocardium region of interest for the strain calculations. For example, a user may interact with the cardiac ultrasound images, which may be displayed to the user via a display device (e.g., the display device 118 of FIG. 1 or the display device 233 of FIG. 2), via a user input device (e.g., the user interface 115 of FIG. 1 or the user input device 232 of FIG. 2). The user may use the user input device to select the myocardium region of interest according to the cardiac ultrasound image displayed on the display device and their knowledge of cardiac structures. The myocardium region of interest may include a defined region having a shape and position on the corresponding cardiac ultrasound image as selected by the user.

At 506, the method 500 includes applying the mask of the pericardium to the cardiac ultrasound images to exclude the pericardium from the cardiac ultrasound images. For example, applying the mask of the pericardium to the cardiac ultrasound images to exclude the pericardium from the cardiac ultrasound images may include overlaying the mask on the corresponding cardiac ultrasound image to align the mask with the cardiac ultrasound image in terms of location (e.g., position) on the cardiac ultrasound image. Doing so may reversibly exclude the pericardium from being depicted in the cardiac ultrasound image, such as by reversibly removing pixel information within the mask. For example, reversibly removing the pixel information within the mask may include setting pixel values within the mask to zero while the mask is applied to the corresponding cardiac ultrasound image.

In some examples, some region(s) of the pericardium may overlap with the myocardium region of interest. For example, overlaying the mask on the corresponding cardiac ultrasound image may align portion(s) of the mask with portion(s) of the myocardium region of interest. As such, the portion(s) of the mask that align with the portion(s) of the myocardium region of interest may remove the region(s) of the pericardium in the myocardium region of interest. It may be understood that in some examples, there may not be overlap between the mask of the pericardium with the myocardium region of interest, such as when the user selection of the myocardium region of interest does not include any portion(s) of the pericardium.

In some embodiments, the method 500 may include outputting an alert in response to at least a threshold amount of overlap between the pericardium mask and the myocardium region of interest. The threshold amount of overlap may be a non-zero pre-determined percentage of the myocardium region of interest that includes the pericardium mask, for example. Alternatively, the threshold amount of overlap may be a non-zero pre-determined percentage of the pericardium mask that overlaps with the myocardium region of interest. The threshold amount of overlap may correspond to an amount of overlap above which an accuracy of the strain analysis may be decreased due to the positioning of the myocardium region of interest in relation to the pericardium mask. For example, although the pericardium is excluded via the mask, a relatively large portion of the myocardium may be undesirably excluded from the myocardium region of interest due to the positioning of the myocardium region of interest in relation to the pericardium mask and thus not analyzed. The alert may be an audible and/or visual alert. For example, the alert may include one or more of an audible sound, a message (e.g., output to the display device and/or read aloud via the user interface), and a graphic (such as an icon output to the display device).

In one example, in addition to the alert, instructions to reposition the myocardium region of interest may be output to the operator, such as via a message output to the display device. In another example, the instructions may inform the operator to select another cardiac ultrasound image for the strain analysis because the current one is not optimal. In some embodiments, a first alert and a first set of instructions to reposition the ROI may be output in response to a first, lower threshold amount of overlap (e.g., 20%) between the pericardium mask and the myocardium region of interest, and a second, different alert and a second set of instructions to select another cardiac ultrasound image may be output in response to a second, higher threshold amount of overlap (e.g., 30%) between the pericardium mask and the myocardium region of interest.

At 508, the method 500 includes performing speckle tracking echocardiography on the myocardium region of interest with the pericardium excluded via the mask. For example, the myocardium region of interest depicted in the cardiac ultrasound images may be tracked throughout an entire heart cycle or a portion of the heart cycle to determine how each portion of the myocardium contracts and relaxes through the heart cycle. Each heart cycle comprises one heartbeat, which includes two periods called diastole and systole. During diastole, the myocardium relaxes and the heart refills with blood. During systole, the myocardium contracts to pump the blood out of the heart. The contraction and relaxation cause shortening and elongation of the myocardium, respectfully, which may be quantified via the speckle tracking echocardiography.

The speckle tracking echocardiography may include a pre-programmed analysis tool or algorithm that calculates the strain at a given position of the myocardium region of interest in the cardiac ultrasound images as a change in length of the heart muscle at the given position between two time points. Thus, the strain at the given position may change throughout the heart cycle as the muscle expands and contracts. Further, strain values may be determined in a plurality of directions (e.g., longitudinal, circumferential, and radial) that correspond to the change in length in the corresponding direction. For example, a longitudinal strain value may denote a change in length of the heart muscle along its long axis, a circumferential strain value may denote a circumferential change of the associated cavity (e.g., chamber) during the heart cycle, and a radial strain value may denote a change in length of the muscle wall along its radius (e.g., a change in thickness). Each strain value may be given as a percentage change (e.g., negative or positive) between an initial time point (e.g., before an electrical pulse through the heart causes contraction) and a final time point (e.g., after the electrical pulse through the heart causes contraction), for example. Further, the speckle tracking echocardiography algorithm may generate one or both of regional strain values corresponding to a portion of the myocardium region of interest for a plurality of portions and global strain values corresponding to an entirety of the myocardium region of interest.

As one example, the speckle tracking echocardiography may include defining brighter pixel "speckles" depicted within the myocardium region of interest that are produced as a result of the scatter of the ultrasound beam by the tissue. The identified speckles may be tracked frame-by-frame to determine a change in their position in different dimensions (e.g., longitudinal, circumferential, and radial). As an illustrative example, the speckle tracking echocardiography may use a sum-of-the absolute-differences algorithm. The speckle tracking echocardiography may further determine a magnitude of myocardial deformation in these different directions over the heart cycle, corresponding to mechanical movement of the heart, to generate the strain values, which may be given as a percentage change (e.g., negative values for contraction and positive values for expansion). In some examples, the speckle tracking echocardiography may further generate strain rate curves corresponding to a rate of change in the strain values over time (e.g., over the heart cycle).

As noted above, because the pericardium is excluded from the cardiac ultrasound images via the mask, any region(s) of the pericardium included in the myocardium region of interest will not be analyzed via the speckle tracking echocardiography algorithm. For example, because the pixel information is removed from the identified pericardium via the mask, no brighter pixel speckles will be identified within the pericardium and tracked to determine the strain values. That is, portions of the myocardium region of interest overlapping with the pericardium mask (e.g., pixels of the cardiac ultrasound images that are included by both of the myocardium region of interest and the pericardium mask) are not analyzed via the speckle tracking echocardiography. Thus, the speckle tracking echocardiography is performed using pixels of the cardiac ultrasound images within the defined myocardium region of interest while excluding the pixels of the ultrasound images that are included within the defined pericardium mask.

At 510, the method 500 includes outputting the strain values and/or a strain map. The speckle tracking echocardiography quantifies the deformation of the myocardium at various locations in time, as mentioned above. As such, the strain map may show a strength (e.g., a magnitude and direction) of the deformation at a given portion the myocardium region of interest as an overlay on the myocardium region of interest in the cardiac ultrasound images, which may be output to the display device and/or stored in a memory. For example, negative strain values may indicate contraction, with the magnitude of the negative value increasing as a strength of the contraction increases, whereas positive strain values may indicate elongation, with the magnitude of the positive value increasing as the strength of the contraction increases. Example display outputs are shown in FIGS. 10-11, as will be described below. Additionally or alternatively, the strain values may be output via a series of numbers, a graphic showing the strain values over time, or another type of visual representation of the strain values. The method 500 may then end.

Figure 6:
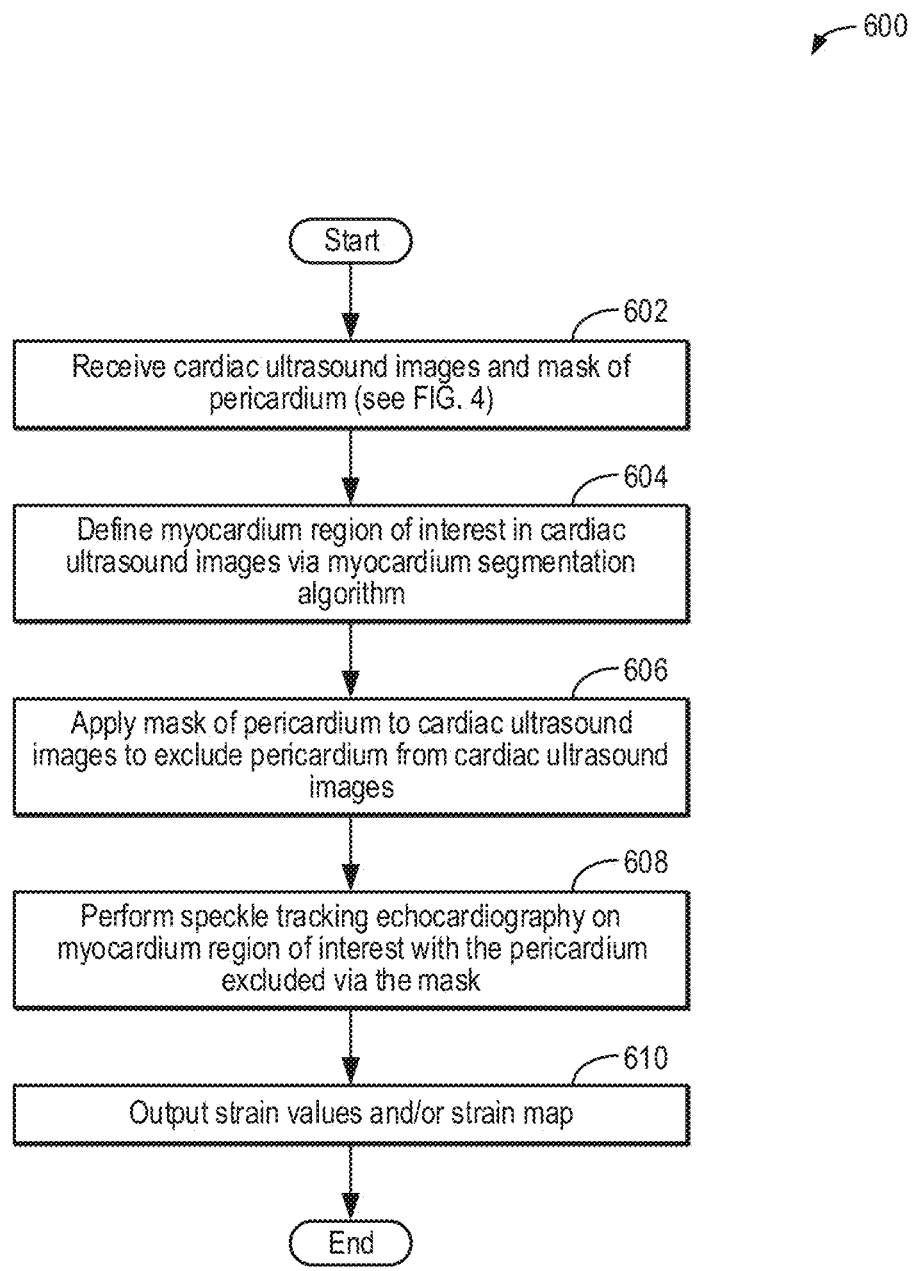
FIG. 6 shows a flow chart of an example method for calculating cardiac strain values by excluding regions within a generated pericardium mask, according to another embodiment.

Referring now to FIG. 6, an example method 600 for calculating cardiac strain values while excluding regions within a generated pericardium mask is shown. The method 600 provides a second embodiment of performing the strain value calculations. In some embodiments, the method 600 may be performed as a part of the method 400 of FIG. 4 (e.g., at 410). In other embodiments, the method 600 may be executed separately and use cardiac ultrasound images and a mask of the pericardium generated by another method, such as the method 400 of FIG. 4. The method 600 is similar to the method 500 of FIG. 5, as described above. Thus, for brevity, differences between the method 500 and the method 500 will be described below.

At 602, the method 600 includes receiving cardiac ultrasound images and the mask of the pericardium, such as generated via the method 400 of FIG. 4 and as described above at 502 of FIG. 5.

At 604, the method 600 includes defining a myocardium region of interest in the cardiac ultrasound images via a myocardium segmentation algorithm. For example, each cardiac ultrasound image may be input into the myocardium segmentation algorithm in substantially real-time, as each ultrasound image is generated from real-time ultrasound imaging data. Alternatively, each cardiac ultrasound image may be processed by the myocardium segmentation algorithm offline, after the ultrasound imaging data acquisition is finished. In some embodiments, the myocardium segmentation algorithm may be included in a cardiac segmentation module, such as the cardiac segmentation module 212 described above with respect to FIG. 2. The myocardium segmentation algorithm may include one or more image recognition algorithms, shape detection algorithms, and/or edge detection algorithms for distinguishing the myocardium from other tissues and/or structures of the heart, including the pericardium. The myocardium segmentation algorithm may further include one or more machine learning algorithms and/or traditionally programmed algorithms for identifying and segmenting the myocardium. For example, the myocardium may be identifiable based on its relative positioning in the ultrasound images. Further, the myocardium may be divided into a right ventricle portion, a right atrium portion, a left ventricle portion, and a left atrium portion of cardiac muscle surrounding each chamber of the heart, at least in some embodiments. For example, the chambers may be identifiable based on their relative positioning in the ultrasound images and pixel contrast between the brighter (e.g., higher intensity) pixels of the myocardium and the darker (e.g., lower intensity) pixels of the blood-filled chambers.

The myocardium region of interest may include a defined region having a shape and position on the corresponding cardiac ultrasound image selected by the myocardium segmentation algorithm according to the ability of the myocardium segmentation algorithm to distinguish the myocardium from other heart tissues. It may be understood that in some embodiments, the myocardium region of interest may be further defined or adjusted based on user input, such as described above with respect to FIG. 3.

At 606, the method 600 includes applying the mask of the pericardium to the cardiac ultrasound images to exclude the pericardium from the cardiac ultrasound images, such as described above at 506 of FIG. 5. At 608, the method 600 includes performing speckle tracking echocardiography on the myocardium region of interest with the with the pericardium excluded via the mask, such as described above at 508 of FIG. 5. At 610, the method 600 includes outputting the strain values and/or a strain map, such as described above at 510 of FIG. 5. The method 600 may then end.

In this way, the methods of FIGS. 4-6 may be used to remove pericardium information from the myocardium region of interest of cardiac ultrasound images so that the pericardium information is not used in calculating cardiac strain values. As a result, the strain values may more accurately reflect myocardial deformation during a heart cycle, and so areas of impaired muscle function may be more accurately distinguished from healthy tissue.

Turning now to FIG. 7, a first example display output 700 is shown that includes a cardiac ultrasound image 702. The cardiac ultrasound image 702 is a B-mode grayscale image and shows an APLAX view of a heart. The display output 700 further depicts a myocardium region of interest 704 overlaid on the cardiac ultrasound image 702. The myocardium region of interest 704 is adjacent to a pericardium region 706. In the example shown in FIG. 7, the pericardium region 706 does not overlap with the myocardium region of interest 704. Therefore, even if pericardium masking were not used, the pericardium region 706 may not affect strain calculations performed on the myocardium region of interest 704.

In contrast, FIG. 8 shows a second example display output 800 including a cardiac ultrasound image 802. Similar to the cardiac ultrasound image 702 of FIG. 7, the cardiac ultrasound image 802 is a B-mode grayscale image of an APLAX view of a heart. However, a pericardium region 806 depicted in the cardiac ultrasound image 802 does overlap with a myocardium region of interest 804 overlaid on the cardiac ultrasound image 802. Therefore, if the pericardium region 806 were not removed via masking, such as according to the methods of FIGS. 4-6, then strain calculations performed on the myocardium region of interest 804 will include information from the pericardium region 806, which may result in both regional and global strain values being underestimated.

For example, FIG. 9 shows a third display output 900 including a cardiac ultrasound image 902. The display output 700 further depicts a myocardium region of interest 904 and a pericardium region 906 within the cardiac ultrasound image 902. The pericardium region 906 overlaps with the myocardium region of interest 904. However, a pericardium mask 908 having a same size and position as the pericardium region 906 on the cardiac ultrasound image 902 is overlaid on the cardiac ultrasound image 902. Thus, despite an area of overlap between the pericardium region 906 and the myocardium region of interest 904, the pericardium mask 908 excludes information from the area of overlap from being used in strain calculations.

The effect of excluding the pericardium from strain value calculations via pericardium masking is illustrated in FIGS. 10 and 11. FIGS. 10 and 11 each show a strain map generated by performing speckle tracking echocardiography on a series of cardiac ultrasound images, including a cardiac ultrasound image 1002. Specifically, FIGS. 10 and 11 each show the strain map as an overlay on the cardiac ultrasound image 1002. Thus, the strain values shown in FIGS. 10 and 11 may be generated from the same series of cardiac ultrasound images.

Referring first to FIG. 10, a first strain map output 1000 is shown, which includes a plurality of strain values 1006 for a myocardium region of interest 1004 as an overlay on the cardiac ultrasound image 1002. The plurality of strain values 1006 are calculated while excluding the pericardium from the myocardium region of interest 1004 via masking, such as according to the methods described above with respect to FIGS. 4-6. The myocardium region of interest 1004 is sub-segmented into a plurality of portions 1004a-1004f. The plurality of strain values 1006 include a first strain value of −20% for a first portion 1004a, a second strain value of −12% for a second portion 1004b, a third strain value of −18% for a third portion 1004c, a fourth strain value of −20% for a fourth portion 1004d, a fifth strain value of −23% for a fifth portion 1004e, and a sixth strain value of −13% for a sixth portion 1004f. Further, a global strain value for the first strain map output 1000 is −16.9%.

In contrast, FIG. 11 shows a second strain map output 1100 including a plurality of strain values 1106 for the myocardium region of interest 1004. The plurality of strain values 1106 are calculated without excluding the pericardium from the myocardium region of interest 1004 via masking, and thus, the non-contractile nature of the pericardium affects the plurality of strain values 1106. The plurality of strain values 1106 include a first strain value of 4% for the first portion 1004a, a second strain value of 7% for the second portion 1004b, a third strain value of −15% for the third portion 1004c, a fourth strain value of −24% for the fourth portion 1004d, a fifth strain value of −23% for the fifth portion 1004e, and a sixth strain value of −13% for the sixth portion 1004f. In particular, by including the pericardium in the strain calculations instead of excluding the pericardium via the pericardium mask, the strain values for the first portion 1004a and the second portion 1006b are positive instead of negative. Further, a global strain value for the second strain map output 1100 is −11.6%, which is a lower magnitude than the global strain value of −16.9% for the first strain map output 1000 of FIG. 10.

These positive strain calculations are incorrect due to the effect of the pericardium on the strain value calculations, but the positive values themselves are not indicative of the pericardium being analyzed. Thus, a user may not be able to distinguish between incorrect strain values due to including the pericardium and strain values that are positive due to impaired muscle function.

By automatically generating the pericardium mask and using it to exclude pericardium information from the myocardium region of interest while performing strain value calculations, the user is not faced with determining whether or not the strain values are positive due to error or due to impaired tissue function. As a result, areas of weak heart muscle or dead tissue may be more easily identified. By more easily identifying areas of weak heart muscle or dead tissue, a time to diagnosis may be decreased, enabling faster patient interventions for more positive patient outcomes.

A technical effect of generating a mask of the pericardium and applying the mask to cardiac ultrasound images while performing speckle tracking echocardiography is that strain values may be more accurately calculated with a reduced reliance on user expertise.

The disclosure also provides support for a method, comprising: generating cardiac ultrasound images from ultrasound imaging data of a heart, excluding pericardium depicted in the cardiac ultrasound images, and calculating strain values of a myocardium region of interest in the cardiac ultrasound images while excluding the pericardium depicted in the cardiac ultrasound images. In a first example of the method, excluding the pericardium depicted in the cardiac ultrasound images comprises: identifying the pericardium depicted in the cardiac ultrasound images, segmenting the pericardium depicted in the cardiac ultrasound images, generating a mask of the pericardium from the identified and segmented pericardium, and applying the mask of the pericardium to the cardiac ultrasound images. In a second example of the method, optionally including the first example, each of identifying the pericardium depicted in the cardiac ultrasound images and segmenting the pericardium depicted in the cardiac ultrasound images is via a pericardium segmentation algorithm. In a third example of the method, optionally including one or both of the first and second examples, calculating the strain values of the myocardium region of interest in the cardiac ultrasound images while excluding the pericardium depicted in the cardiac ultrasound images comprises: calculating the strain values by performing speckle tracking echocardiography on the myocardium region of interest of the cardiac ultrasound images having the mask of the pericardium applied. In a fourth example of the method, optionally including one or more or each of the first through third examples, calculating the strain values by performing the speckle tracking echocardiography on the myocardium region of interest having the mask of the pericardium applied comprises determining a positional change in a speckle identified in of the myocardium region of interest between consecutive image frames of the cardiac ultrasound images having the mask of the pericardium applied. In a fifth example of the method, optionally including one or more or each of the first through fourth examples, applying the mask of the pericardium to the cardiac ultrasound images sets pixel values of the cardiac ultrasound images to zero within the mask of the pericardium while the pixel values of the cardiac ultrasound images outside of the mask of the pericardium remain unchanged. In a sixth example of the method, optionally including one or more or each of the first through fifth examples, the strain values comprise one or more of a longitudinal strain value, a circumferential strain value, and a radial strain value. In a seventh example of the method, optionally including one or more or each of the first through sixth examples, the myocardium region of interest is selected via one or both of a myocardium segmentation algorithm and user input. In an eighth example of the method, optionally including one or more or each of the first through seventh examples, the method further comprises: outputting the strain values of the myocardium region of interest to a display device. In a ninth example of the method, optionally including one or more or each of the first through eighth examples, outputting the strain values of the myocardium region of interest to the display device comprises outputting a strain map having the strain values overlaid on the myocardium region of interest according to a spatial position of each strain value on the myocardium region of interest.

The disclosure also provides support for a method, comprising: generating cardiac ultrasound images from ultrasound imaging data of a heart, generating a mask of pericardium from the cardiac ultrasound images via a pericardium segmentation algorithm, applying the mask of the pericardium to the cardiac ultrasound images, determining strain values of a myocardium region of interest in the cardiac ultrasound images while excluding the pericardium from the cardiac ultrasound images via the mask of the pericardium, and outputting the strain values. In a first example of the method, the myocardium region of interest is defined in the cardiac ultrasound images via at least one of a myocardium segmentation algorithm and a user selection. In a second example of the method, optionally including the first example, determining the strain values of the myocardium region of interest in the cardiac ultrasound images while excluding the pericardium from the cardiac ultrasound images via the mask of the pericardium comprises performing speckle tracking echocardiography on the myocardium region of interest in the cardiac ultrasound images while applying the mask of the pericardium to the cardiac ultrasound images. In a third example of the method, optionally including one or both of the first and second examples, the strain values comprise a longitudinal strain value corresponding to a length change in a given portion of the myocardium region of interest during a heart cycle, a circumferential strain value corresponding to a circumference change of an associated chamber of the given portion of the myocardium region of interest during the heart cycle, and a radial strain value corresponding to a change in thickness of the given portion of the myocardium region of interest along its radius during the heart cycle. In a fourth example of the method, optionally including one or more or each of the first through third examples, outputting the strain values comprises at least one of storing the strain values to in a memory and a visual representation of the strain values via a display device.

The disclosure also provides support for a system, comprising: an ultrasound probe, a display device, and a processor configured to execute instructions stored in non-transitory memory that, when executed, cause the processor to: acquire ultrasound imaging data of a heart via the ultrasound probe, generate cardiac ultrasound images from the acquired ultrasound imaging data of the heart, generate a mask of pericardium identified in the cardiac ultrasound images via a pericardium segmentation algorithm, determine cardiac strain values in a myocardium region of interest in the cardiac ultrasound images while the mask of the pericardium is applied to the cardiac ultrasound images, and output the cardiac strain values on the display device. In a first example of the system, to determine the cardiac strain values in the myocardium region of interest in the cardiac ultrasound images while the mask of the pericardium is applied to the cardiac ultrasound images, the processor is configured to execute further instructions stored in the non-transitory memory that, when executed, cause the processor to: apply the mask of the pericardium to the cardiac ultrasound images, define the myocardium region of interest in the cardiac ultrasound images based on one or a combination of output from a myocardium segmentation algorithm and user input, and perform speckle tracking echocardiography on the myocardium region of interest in the cardiac ultrasound images while the mask of the pericardium is applied. In a second example of the system, optionally including the first example, applying the mask of the pericardium to the cardiac ultrasound images non-destructively removes pixel information from a region of each of the cardiac ultrasound images overlapping with the mask so that when the mask of the pericardium is removed, the pixel information is restored. In a third example of the system, optionally including one or both of the first and second examples, applying the mask of the pericardium to the cardiac ultrasound images reversibly sets pixel values within the mask of the pericardium to zero, and wherein the processor is configured to execute further instructions stored in the non-transitory memory that, when executed, cause the processor to: remove the mask of the pericardium from the cardiac ultrasound images after performing the speckle tracking echocardiography on the myocardium region of interest, store the cardiac ultrasound images without the mask of the pericardium applied and the cardiac strain values to memory. In a fourth example of the system, optionally including one or more or each of the first through third examples, to perform the speckle tracking echocardiography on the myocardium region of interest in the cardiac ultrasound images while the mask of the pericardium is applied, the processor is configured to execute further instructions stored in the non-transitory memory that, when executed, cause the processor to: define brighter pixel speckles within the myocardium region of interest, track displacement of the brighter pixel speckles between an initial time point of the cardiac ultrasound images and a final time point of the cardiac ultrasound images, and calculate the cardiac strain values for a plurality of portions of the myocardium region of interest based on the displacement of the brighter pixel speckles in each of the plurality of portions in each of a longitudinal direction, a radial direction, and a circumferential direction.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
generating cardiac ultrasound images from ultrasound imaging data of a heart;
segmenting pericardium depicted in the cardiac ultrasound images and applying a pericardium mask to the pericardium segmented in the cardiac ultrasound images;
excluding the pericardium depicted in the cardiac ultrasound images by excluding the masked pericardium; and
calculating strain values of a myocardium region of interest in the cardiac ultrasound images while excluding the masked pericardium depicted in the cardiac ultrasound images.

2. The method of claim 1, wherein segmenting the pericardium depicted in the cardiac ultrasound images is carried out via a pericardium segmentation algorithm, and wherein the pericardium is identified based on a relative positioning in the cardiac ultrasound images and a pixel contrast between brighter pixels of the pericardium compared with the dimmer pixels of myocardium neighboring the pericardium.

3. The method of claim 1, wherein calculating the strain values of the myocardium region of interest in the cardiac ultrasound images while excluding the masked pericardium depicted in the cardiac ultrasound images comprises:
calculating the strain values by performing speckle tracking echocardiography on the myocardium region of interest of the cardiac ultrasound images having the pericardium mask applied.

4. The method of claim 3, wherein calculating the strain values by performing the speckle tracking echocardiography on the myocardium region of interest having the pericardium mask applied comprises determining a positional change in a speckle identified in of the myocardium region of interest between consecutive image frames of the cardiac ultrasound images having the pericardium mask applied.

5. The method of claim 1, wherein applying the pericardium mask to the cardiac ultrasound images sets pixel values of the cardiac ultrasound images to zero within the pericardium mask while the pixel values of the cardiac ultrasound images outside of the pericardium mask remain unchanged.

6. The method of claim 1, wherein the strain values comprise one or more of a longitudinal strain value, a circumferential strain value, and a radial strain value.

7. The method of claim 1, wherein the myocardium region of interest is selected via one or both of a myocardium segmentation algorithm and user input, and wherein the pericardium mask is generated by setting pixel values in a region identified as the pericardium to zero and pixel values in all other areas that do not include the pericardium are set to one.

8. The method of claim 1, further comprising:
outputting the strain values of the myocardium region of interest to a display device.

9. The method of claim 8, wherein outputting the strain values of the myocardium region of interest to the display device comprises outputting a strain map having the strain values overlaid on the myocardium region of interest according to a spatial position of each strain value on the myocardium region of interest.

10. A method, comprising:
generating cardiac ultrasound images from ultrasound imaging data of a heart;
generating a mask of pericardium from the cardiac ultrasound images via a pericardium segmentation algorithm;
applying the mask of the pericardium to the cardiac ultrasound images;
determining strain values of a myocardium region of interest in the cardiac ultrasound images while excluding the pericardium from the cardiac ultrasound images via the mask of the pericardium, wherein the pericardium overlaps with the myocardium region of interest; and
outputting the strain values.

11. The method of claim 10, wherein the myocardium region of interest is defined in the cardiac ultrasound images via at least one of a myocardium segmentation algorithm and a user selection.

12. The method of claim 10, wherein determining the strain values of the myocardium region of interest in the cardiac ultrasound images while excluding the pericardium from the cardiac ultrasound images via the mask of the pericardium comprises performing speckle tracking echocardiography on the myocardium region of interest in the cardiac ultrasound images while applying the mask of the pericardium to the cardiac ultrasound images.

13. The method of claim 10, wherein the strain values comprise a longitudinal strain value corresponding to a length change in a given portion of the myocardium region of interest during a heart cycle, a circumferential strain value corresponding to a circumference change of an associated chamber of the given portion of the myocardium region of interest during the heart cycle, and a radial strain value corresponding to a change in thickness of the given portion of the myocardium region of interest along its radius during the heart cycle.

14. The method of claim 10, wherein outputting the strain values comprises at least one of storing the strain values to in a memory and a visual representation of the strain values via a display device.

15. A system, comprising:
an ultrasound probe;
a display device; and
a processor configured to execute instructions stored in non-transitory memory that, when executed, cause the processor to:
acquire ultrasound imaging data of a heart via the ultrasound probe;
generate cardiac ultrasound images from the acquired ultrasound imaging data of the heart;
generate a mask of pericardium identified in the cardiac ultrasound images based on the pericardium being separately segmented via a pericardium segmentation algorithm;
determine cardiac strain values in a myocardium region of interest in the cardiac ultrasound images while the mask of the pericardium is applied to the cardiac ultrasound images; and
output the cardiac strain values on the display device.

16. The system of claim 15, wherein to determine the cardiac strain values in the myocardium region of interest in the cardiac ultrasound images while the mask of the pericardium is applied to the cardiac ultrasound images, the processor is configured to execute further instructions stored in the non-transitory memory that, when executed, cause the processor to:

apply the mask of the pericardium to the cardiac ultrasound images;

define the myocardium region of interest in the cardiac ultrasound images based on one or a combination of output from a myocardium segmentation algorithm and user input;

divide the myocardium region of interest into a right ventricle portion, a right atrium portion, a left ventricle portion, and a left atrium portion of cardiac muscle; and perform speckle tracking echocardiography on the myocardium region of interest in the cardiac ultrasound images while the mask of the pericardium is applied.

17. The system of claim 16, wherein applying the mask of the pericardium to the cardiac ultrasound images non-destructively removes pixel information from a region of each of the cardiac ultrasound images overlapping with the mask so that when the mask of the pericardium is removed, the pixel information is restored.

18. The system of claim 16, wherein applying the mask of the pericardium to the cardiac ultrasound images reversibly sets pixel values within the mask of the pericardium to zero, and wherein the processor is configured to execute further instructions stored in the non-transitory memory that, when executed, cause the processor to:

remove the mask of the pericardium from the cardiac ultrasound images after performing the speckle tracking echocardiography on the myocardium region of interest;

store the cardiac ultrasound images without the mask of the pericardium applied and the cardiac strain values to memory.

19. The system of claim 16, wherein to perform the speckle tracking echocardiography on the myocardium region of interest in the cardiac ultrasound images while the mask of the pericardium is applied, the processor is configured to execute further instructions stored in the non-transitory memory that, when executed, cause the processor to:

define brighter pixel speckles within the myocardium region of interest;

track displacement of the brighter pixel speckles between an initial time point of the cardiac ultrasound images and a final time point of the cardiac ultrasound images; and calculate the cardiac strain values for a plurality of portions of the myocardium region of interest based on the displacement of the brighter pixel speckles in each of the plurality of portions in each of a longitudinal direction, a radial direction, and a circumferential direction.

20. The method of claim 10, wherein an area of overlap for the pericardium and the myocardium region of interest is excluded in the determination of the strain values for the myocardium region of interest.

* * * * *